(12) United States Patent
Chmil et al.

(10) Patent No.: US 10,366,208 B1
(45) Date of Patent: Jul. 30, 2019

(54) FACILITATING PRESCRIPTION MANAGEMENT

(71) Applicant: Allscripts Software, LLC, Chicago, IL (US)

(72) Inventors: Igor Chmil, Buffalo Grove, IL (US); Mark Gregory Plunkett, Libertyville, IL (US); Stanislav Makarskyy, Arlington Heights, IL (US)

(73) Assignee: ALLSCRIPTS SOFTWARE, LLC, Raleigh ( * ) Notice: Subject to any disclaimer, the term of this patent is extended or adjusted under 35 U.S.C. 154(b) by 823 days.

(21) Appl. No.: 14/872,109

(22) Filed: Sep. 30, 2015

(51) Int. Cl.
*G06F 19/00* (2018.01)

(52) U.S. Cl.
CPC .............................. *G06F 19/3456* (2013.01)

(58) Field of Classification Search
None
See application file for complete search history.

(56) References Cited

U.S. PATENT DOCUMENTS

| | | | | |
|---|---|---|---|---|
| 7,769,601 B1* | 8/2010 | Bleser | .................. | G06F 19/326 705/3 |
| 7,860,725 B2* | 12/2010 | Gopinathan | ........... | A61B 5/411 705/2 |
| 8,849,449 B2* | 9/2014 | Waugh | ................ | G06F 19/3462 700/234 |
| 2009/0157424 A1* | 6/2009 | Hans | ...................... | G06Q 10/10 705/2 |
| 2011/0257989 A1* | 10/2011 | Kumar | ................... | G06Q 50/22 705/2 |
| 2011/0307265 A1* | 12/2011 | Bannis | ................... | G06Q 50/22 705/2 |
| 2012/0253829 A1* | 10/2012 | John | ...................... | G06Q 50/22 705/2 |
| 2012/0253852 A1* | 10/2012 | Pourfallah | ......... | G06Q 20/3276 705/4 |
| 2017/0147783 A1* | 5/2017 | Carroll | ................... | G06Q 50/22 |

* cited by examiner

*Primary Examiner* — Neal Sereboff
(74) *Attorney, Agent, or Firm* — Medley, Behrens & Lewis, LLC (57) ABSTRACT

Healthcare providers can utilize ePrescribing applications to prescribe electronic prescriptions to patients which will be accessible to patients via a cloud platform. A patient can determine how he or she would like to fill such prescriptions. A patient can search for and select a pharmacy to electronically send a prescription to, or alternatively can choose to receive a scannable copy of the prescription at his or her mobile device for presentation at a pharmacy location. In the latter event, a patient can utilize his or her electronic device to display a scannable code which a pharmacy can scan to access prescription information.

20 Claims, 8 Drawing Sheets

FACILITATING PRESCRIPTION MANAGEMENT

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to prescription management.

Traditionally, when a healthcare provider prescribes a medication for a patient, either the patient is given a written prescription, or a prescription is called in or sent electronically by the healthcare provider to a pharmacy. In the case where a healthcare provider sends an electronic prescription, a patient generally has to decide at the time the prescription is prescribed which retail or mail order pharmacy he or she wants the prescription sent to. Once a prescription is sent to a pharmacy by a healthcare provider, the pharmacy owns the prescription, and the patient cannot thereafter control where the prescription is filled.

A need exists for improvement in prescription management. This need and other needs are addressed by one or more aspects of the present invention.

SUMMARY OF THE INVENTION

The present invention includes many aspects and features. Moreover, while many aspects and features relate to, and are described in, a particular context, the present invention is not limited to use only in this context, as will become apparent from the following summaries and detailed descriptions of aspects, features, and one or more embodiments of the present invention.

Accordingly, one aspect of the present invention relates to a method comprising receiving, at a cloud platform from an ePrescribing application, prescription data for a prescription for a patient prescribed by a healthcare provider using the ePrescribing application; displaying, to the patient via a display screen associated with an electronic device, a first interface configured to allow the patient to select whether to electronically send the prescription to a pharmacy, or receive a scannable copy of the prescription; receiving, from the patient via one or more input devices associated with the electronic device, input corresponding to an indication that the patient wants to electronically send the prescription to a pharmacy; displaying, to the patient via the display screen associated with the electronic device, a second interface configured to allow the patient to select a particular pharmacy to electronically send the prescription to; receiving, from the patient via one or more input devices associated with the electronic device, input corresponding to selection of a first pharmacy that the patient wants to electronically send the prescription to; communicating, from the cloud platform to an electronic device associated with the first pharmacy, data representative of the prescription; and receiving, at the cloud platform from an electronic device associated with the first pharmacy, data indicating that the prescription has been filled.

In a feature of this aspect, the electronic device comprises a desktop computer.

In a feature of this aspect, the electronic device comprises a laptop computer.

In a feature of this aspect, the electronic device comprises a tablet.

In a feature of this aspect, the electronic device comprises a phone.

In a feature of this aspect, the first interface and the second interface are interfaces of a web portal.

In a feature of this aspect, the first interface and the second interface are interfaces of a mobile application.

In a feature of this aspect, the first pharmacy comprises a brick and mortar pharmacy.

In a feature of this aspect, the first pharmacy comprises a mail order pharmacy.

In a feature of this aspect, the first pharmacy comprises an online pharmacy.

In a feature of this aspect, the first pharmacy comprises a chain pharmacy.

In a feature of this aspect, the first pharmacy comprises a particular store of a chain pharmacy.

Another aspect relates to a method comprising receiving, at a cloud platform from an ePrescribing application, prescription data for a prescription for a patient prescribed by a healthcare provider using the ePrescribing application; displaying, to the patient via a display screen associated with an electronic device, a first interface configured to allow the patient to select whether to electronically send the prescription to a pharmacy, or receive a scannable copy of the prescription; receiving, from the patient via one or more input devices associated with the electronic device, input corresponding to an indication that the patient wants to receive a scannable copy of the prescription; displaying, via the display screen associated with the electronic device, a scannable copy of the prescription including a scannable portion configured to provide first data for identifying the prescription; receiving, at the cloud platform from an electronic device associated with a first pharmacy, a request to verify the validity of the prescription based on the first data for identifying the prescription; communicating, from the cloud platform to an electronic device associated with the first pharmacy, an indication of the validity of the prescription; and receiving, at the cloud platform from an electronic device associated with the first pharmacy, data indicating that the prescription has been filled.

In a feature of this aspect, the method further includes scanning, by the first pharmacy using an electronic scanner, the scannable portion of the scannable copy of the prescription.

In a feature of this aspect, the scannable portion comprises a barcode.

In a feature of this aspect, the scannable portion comprises a scannable image.

In a feature of this aspect, the scannable portion comprises a matrix barcode.

In a feature of this aspect, the scannable portion comprises a quick response code.

In a feature of this aspect, the electronic device comprises a mobile device.

Another aspect relates to a method comprising receiving, at a cloud platform from a first ePrescribing application, prescription data for a first prescription for a first patient prescribed by a first healthcare provider using the first ePrescribing application; displaying, to the first patient via a display screen associated with a first electronic device, a first interface configured to allow the first patient to select whether to electronically send the first prescription to a pharmacy, or receive a scannable copy of the first prescription; receiving, from the first patient via one or more input devices associated with the first electronic device, input corresponding to an indication that the first patient wants to electronically send the prescription to a pharmacy; displaying, to the first patient via the display screen associated with the first electronic device, a second interface configured to allow the first patient to select a particular pharmacy to electronically send the prescription to; receiving, from the first patient via one or more input devices associated with the first electronic device, input corresponding to selection of a first pharmacy that the first patient wants to electronically send the prescription to; communicating, from the cloud platform to an electronic device associated with the first pharmacy, data representative of the first prescription; receiving, at the cloud platform from an electronic device associated with the first pharmacy, data indicating that the first prescription has been filled; receiving, at the cloud platform from a second ePrescribing application, prescription data for a second prescription for a second patient prescribed by a second healthcare provider using the second ePrescribing application; displaying, to the second patient via a display screen associated with a second electronic device, a third interface configured to allow the second patient to select whether to electronically send the second prescription to a pharmacy, or receive a scannable copy of the second prescription; receiving, from the second patient via one or more input devices associated with the second electronic device, input corresponding to an indication that the second patient wants to receive a scannable copy of the second prescription; displaying, via the display screen associated with the second electronic device, a scannable copy of the second prescription including a scannable portion configured to provide first data for identifying the second prescription; receiving, at the cloud platform from an electronic device associated with a second pharmacy, a request to verify the validity of the second prescription based on the first data for identifying the second prescription; communicating, from the cloud platform to an electronic device associated with the second pharmacy, an indication of the validity of the second prescription; and receiving, at the cloud platform from an electronic device associated with the second pharmacy, data indicating that the second prescription has been filled.

In a feature of this aspect, the first patient and the second patient are different patients.

In a feature of this aspect, the first patient and the second patient are the same patient.

In a feature of this aspect, the first healthcare provider and the second healthcare provider are different healthcare providers.

In a feature of this aspect, the first healthcare provider and the second healthcare provider are the same healthcare provider.

In a feature of this aspect, the first pharmacy and the second pharmacy are different pharmacies.

In a feature of this aspect, the first pharmacy and the second pharmacy are the same pharmacy.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. 112, paragraph 6 or subsection (f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

In accordance with one or more preferred implementations, a cloud based prescription repository allows patients to interact with prescriptions provided to them by a healthcare provider. Preferably, a cloud platform is provided which is configured for interaction with healthcare providers, patients, and pharmacies.

Figure 1:
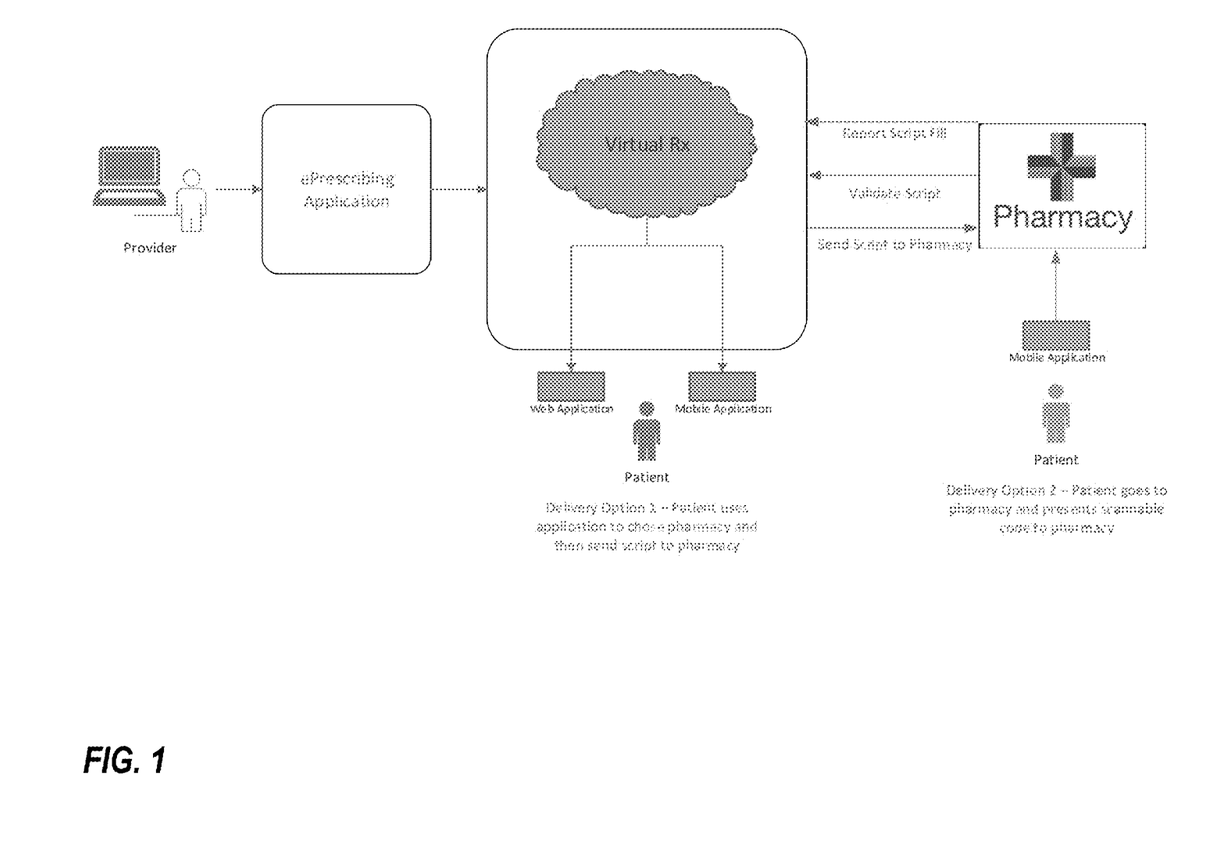
FIG. 1 illustrates exemplary interaction flows for an exemplary system in accordance with one or more preferred implementations.

FIG. 1 illustrates exemplary interaction flows for an exemplary system in accordance with one or more preferred implementations. Preferably, healthcare providers can utilize ePrescribing applications to prescribe electronic prescriptions to patients which will be accessible to patients via the cloud platform. Data regarding these electronic prescriptions will be communicated from an ePrescribing application to the cloud platform.

Preferably, patients can subsequently access prescription information for themselves via a portal or application providing access to the cloud platform. This might comprise, for example, a web portal accessible via a web browser, or a mobile application. Preferably, such a portal or application provides functionality to allow a patient to view prescriptions he or she has been prescribed by a healthcare provider, and further allow a patient to determine how he or she would like to fill such prescriptions. In one or more preferred implementations, a patient can search for and select a pharmacy to electronically send a prescription to, or alternatively can choose to receive a scannable copy of the prescription at his or her mobile device for presentation at a pharmacy location. In the latter event, a mobile application on the patient's device is configured to display a scannable code which a pharmacy can scan to access prescription information.

In either event, pharmacies are able to utilize prescription information, received either via an electronic prescription submission or via a scanned code, to communicate with the cloud platform and validate the prescription, and then subsequently report that the prescription has been successfully filled.

Figure 2:
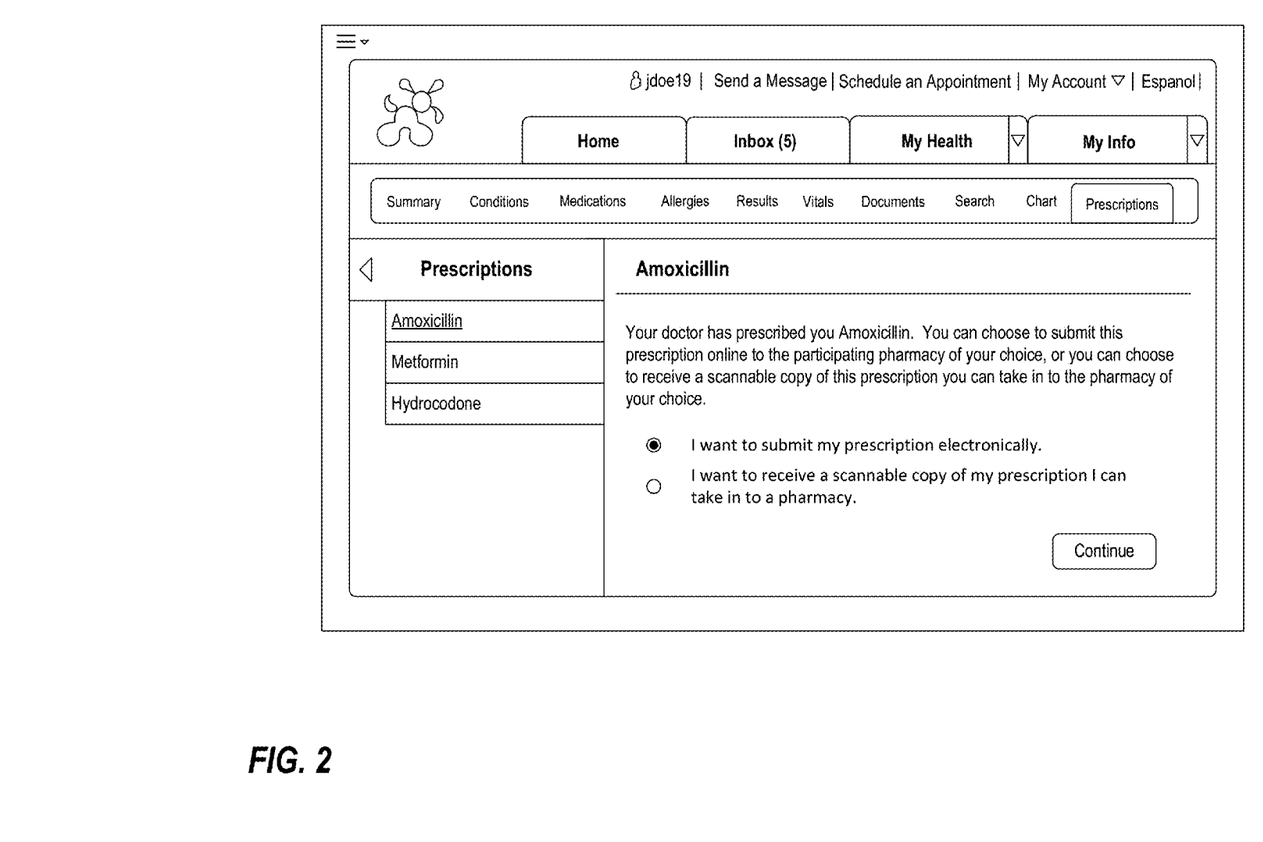
FIG. 2 illustrates an exemplary interface of a patient web portal in accordance with one or more preferred implementations.

FIG. 2 illustrates an exemplary interface of a patient web portal in accordance with one or more preferred implementations. The exemplary interface is prompting a user to indicate how he would like to fill a prescription for Amoxicillin. The user is given a choice between submitting his prescription electronically, and receiving a scannable copy of the prescription that he can take in to a pharmacy.

Figure 3:
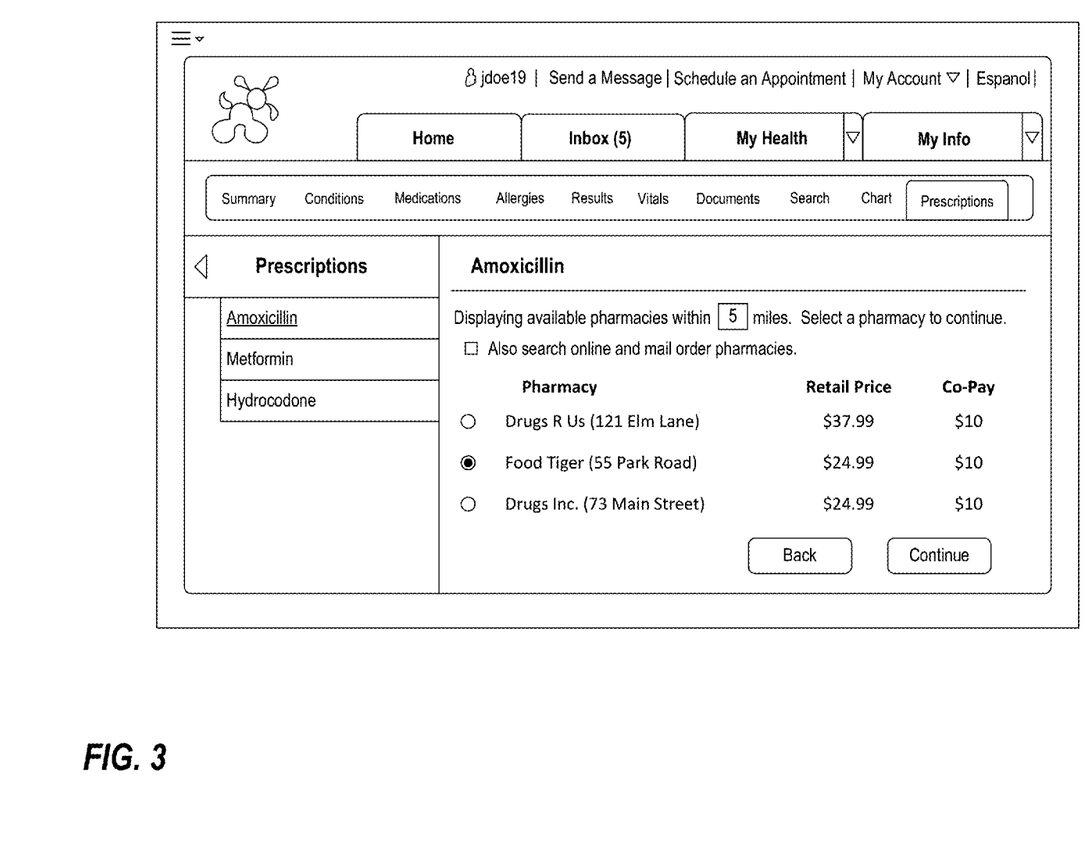
FIG. 3 illustrates an exemplary interface that a user accesses after selecting to submit his or her prescription electronically.

FIG. 3 illustrates an exemplary interface that the user accesses after selecting to submit his prescription electronically. The interface allows the user to search for available brick and mortar, online, and mail order pharmacies. The exemplary interface allows the user to search for pharmacies within a certain distance of his profile's home address, but in one or more preferred implementations other search schemes may additionally or alternatively be utilized.

In accordance with one or more preferred implementations, an interface displays available pharmacies together with retail pricing for the prescription and copay information for the patient, as illustrated in FIG. 3. This allows a user to utilize pricing information to select a pharmacy to send his or her prescription to.

Figure 4:
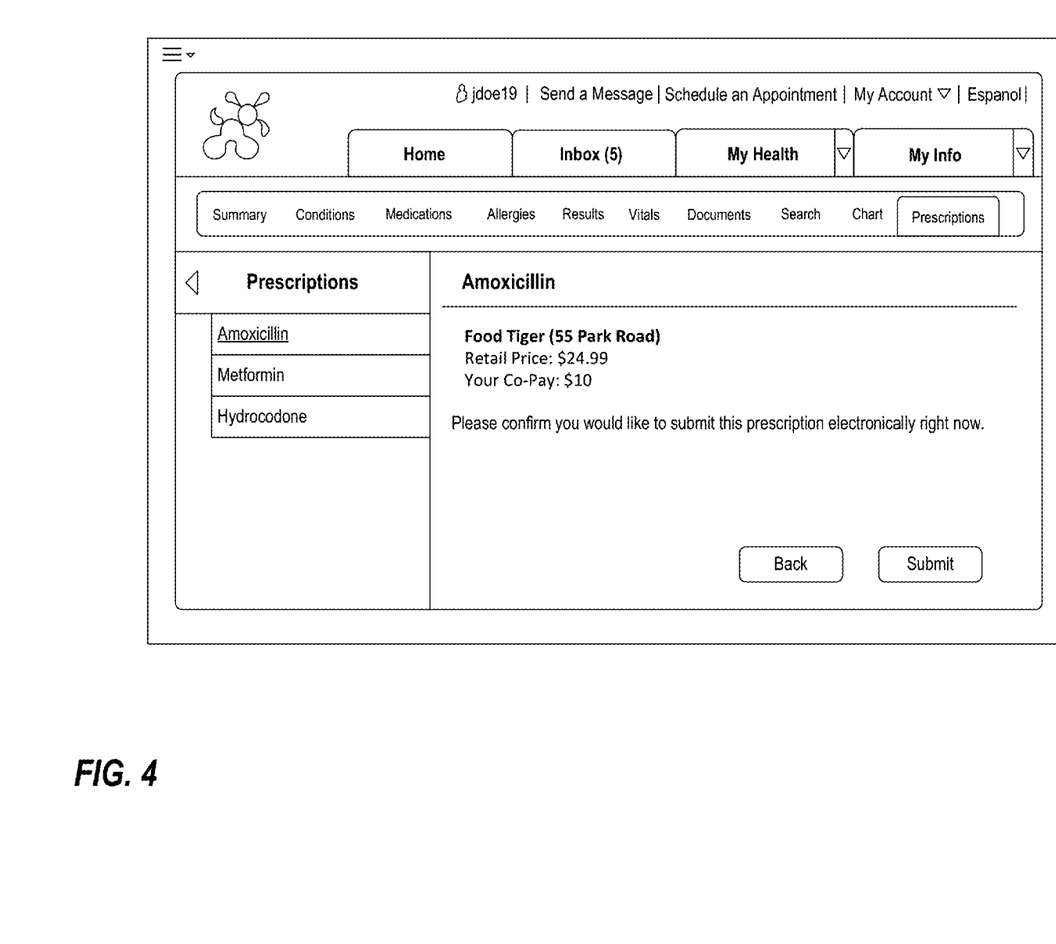
FIG. 4 illustrates an exemplary interface that a user accesses after selecting to submit his or her prescription electronically to a Food Tiger pharmacy.

FIG. 4 illustrates an exemplary interface that a user accesses after selecting to submit his prescription electronically to a Food Tiger pharmacy located at 55 Park Road. The user is prompted to confirm electronic submission of his prescription to this pharmacy.

Figure 5:
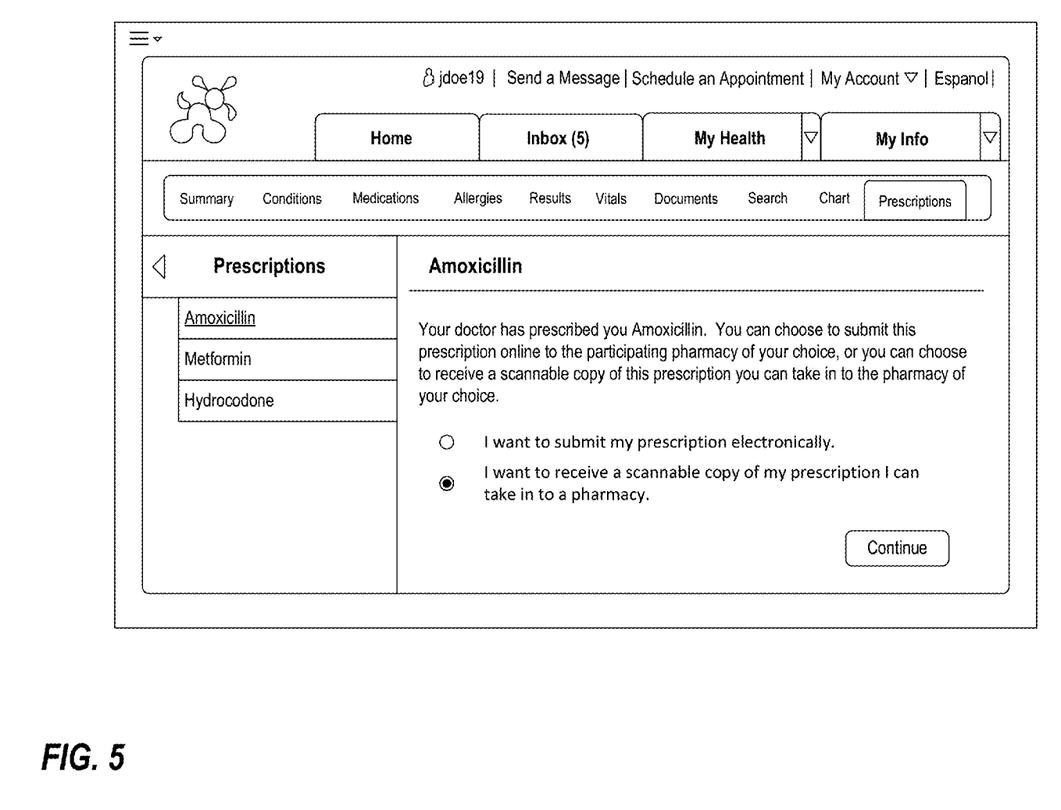
FIG. 5 illustrates user selection of an option to receive a scannable copy of his or her prescription.

If the user does not want to electronically submit his prescription, the user can return to the interface of FIG. 2 and select to receive a scannable copy of his prescription, as illustrated in FIG. 5.

Figure 6:
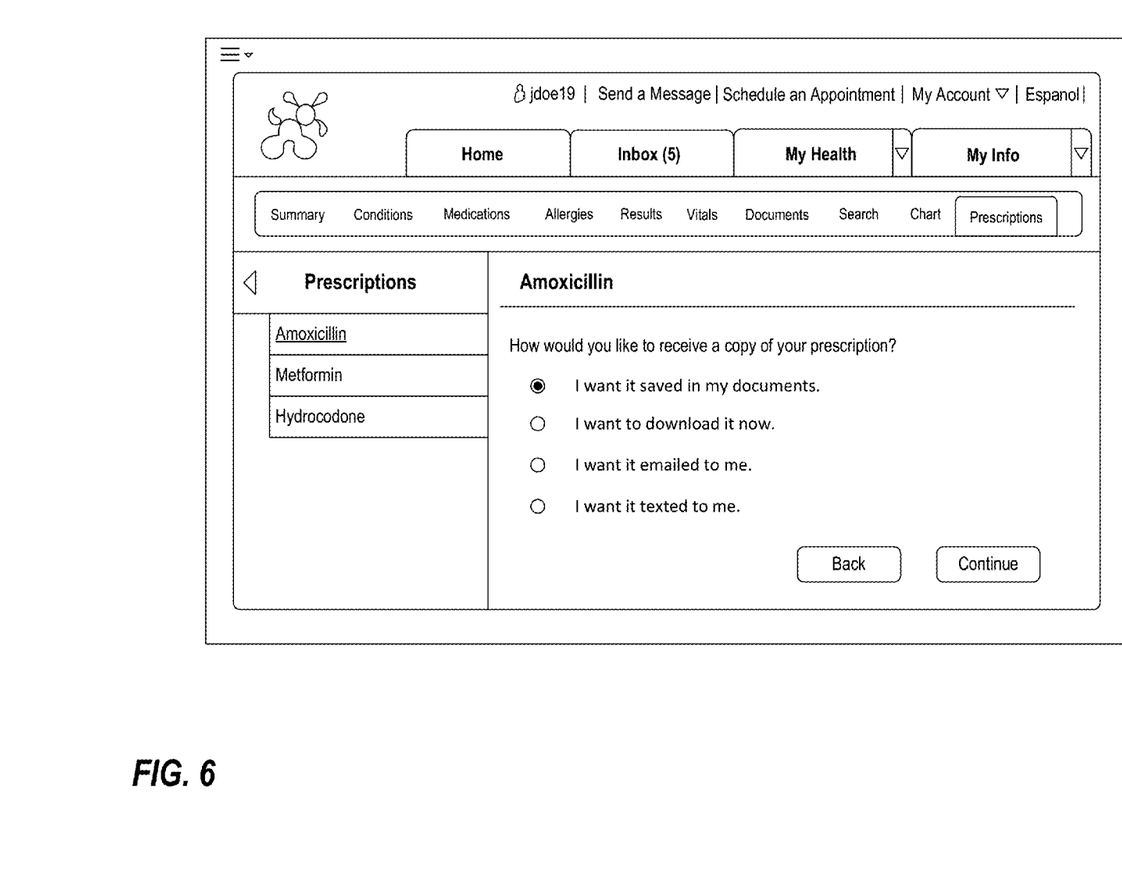
FIG. 6 illustrates an exemplary interface that a user accesses after selecting to receive a scannable copy of his or her prescription.

FIG. 6 illustrates an exemplary interface that a user accesses after selecting to receive such a scannable copy. The exemplary interface of FIG. 6 allows a user to elect to have a scannable copy saved in a documents area associated with his account, to elect to download a scannable copy, or to elect to have a scannable copy texted or emailed, either to a number or address saved in his profile in association with his account, or to a number or address he specifies.

Figure 7:
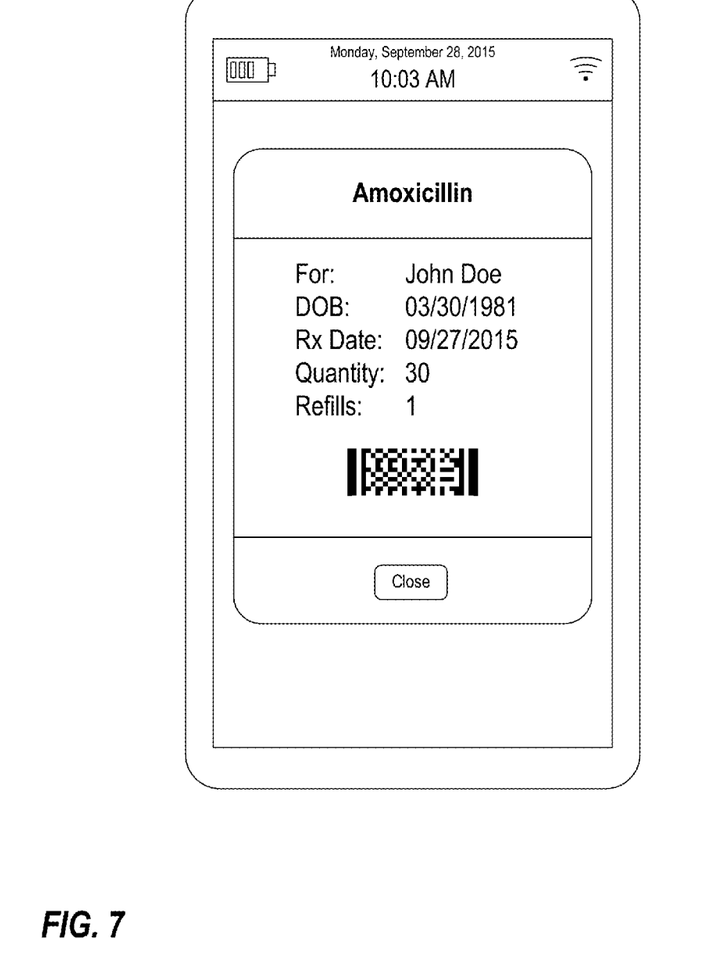
FIG. 7 illustrates display, on the screen of a mobile device of a scannable copy of a prescription.

Such a scannable copy can then be accessed at a mobile device, either as a document that was downloaded, or as a document saved in association with his account, or as a document received via email or text message, and presented onscreen of the mobile device to a pharmacy for scanning, as illustrated in FIG. 7.

Figure 8:
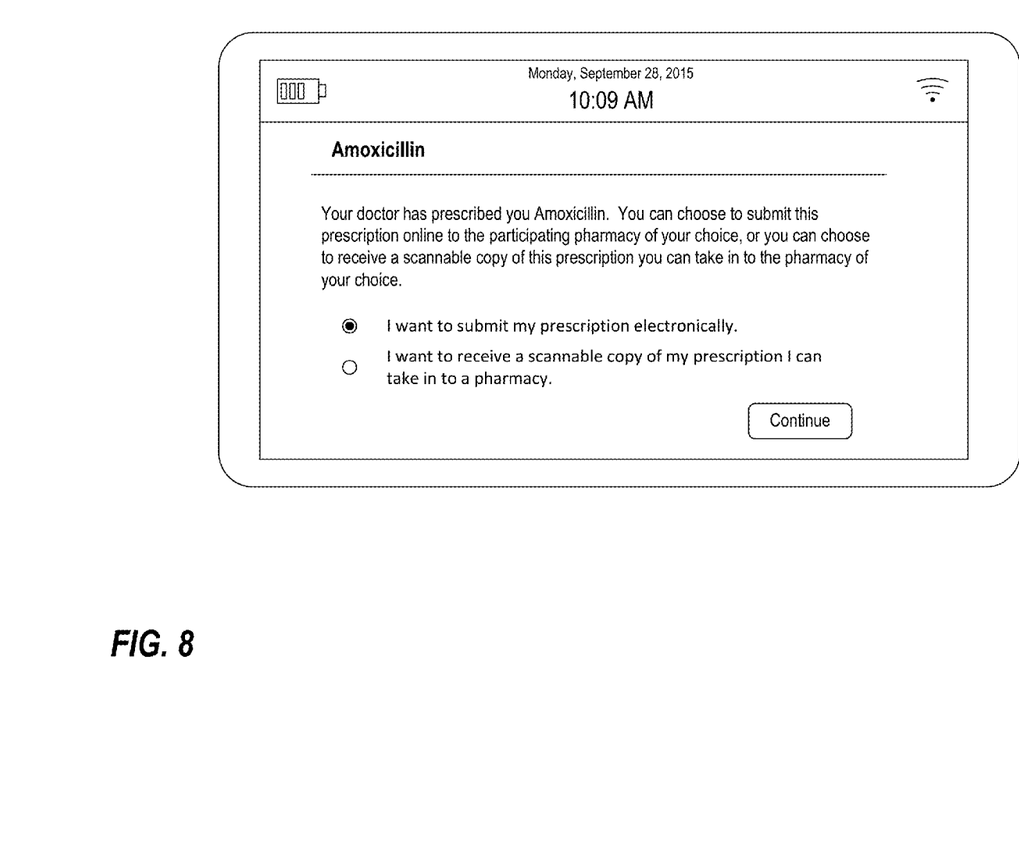
FIG. 8 illustrates prescription management functionality of a mobile application.

Although the interfaces of FIGS. 2-6 represent interfaces of a web portal, in one or more preferred implementations such functionality is additionally or alternatively provided by a mobile application accessible on a mobile device, as illustrated in FIG. 8.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method executed by a cloud platform that is in network communication with an ePrescribing application and a first electronic device operated by a patient, the method comprising:
   receiving, at the cloud platform from the ePrescribing application, an electronic prescription for the patient prescribed by a healthcare provider;
   transmitting first data to the first electronic device, wherein the first data causes a first interface to be displayed on a display screen of the first electronic device, wherein the first interface comprises:
      a first selectable button indicating that the electronic prescription is to be transmitted by the cloud platform to a pharmacy and
      a second selectable button indicating that a scannable copy of the electronic prescription is to be transmitted by the cloud platform to the first electronic device,
   wherein the first electronic device receives a selection of the second selectable button causing the first electronic device to transmit data indicative of the selection of the second selectable button to the cloud platform;
   transmitting second data to the first electronic device, wherein the second data causes the first electronic device to display a second interface on the display screen, wherein the second interface comprises a scannable copy of the electronic prescription including a scannable portion configured to provide identifying data for the electronic prescription, and further wherein an electronic scanner of a first pharmacy scans the scannable portion of the scannable copy of the electronic prescription;
   receiving, at the cloud platform from a second electronic device of the first pharmacy, a request to verify validity of the electronic prescription based on the identifying data for the electronic prescription, wherein the request includes the identifying data for the electronic prescription;
   responsive to verifying the electronic prescription, communicating, from the cloud platform to the second electronic device of the first pharmacy, an indication that the electronic prescription is valid; and
   receiving, at the cloud platform from the second electronic device of the first pharmacy, data indicating that the electronic prescription has been filled by the first pharmacy.

2. The method of claim 1, wherein the scannable portion comprises a barcode.

3. The method of claim 1, wherein the scannable portion comprises a scannable image.

4. The method of claim 1, wherein the scannable portion comprises a matrix barcode.

5. The method of claim 1, wherein the scannable portion comprises a quick response code.

6. The method of claim 1, wherein the first electronic device comprises a mobile device.

7. The method of claim 1, wherein the first electronic device comprises a phone.

8. A method executed by a cloud platform that is in network communication with a first ePrescribing application, a second ePrescribing application, a first electronic device operated by a first patient, and a second electronic device operated by a second patient, the method comprising:
   receiving, at the cloud platform from the first ePrescribing application, a first electronic prescription for the first patient prescribed by a first healthcare provider;
   transmitting first data to the first electronic device, wherein the first data causes the first electronic device to display a first interface on a display screen of the first electronic device, wherein the first interface comprises:
      a first selectable button indicating that the first electronic prescription is to be transmitted by the cloud platform to a pharmacy and
      a second selectable button indicating that a scannable copy of the first electronic prescription is to be transmitted by the cloud platform to the first electronic device,
   wherein the first electronic device receives a selection of the first selectable button causing the first electronic device to transmit data indicative of the selection of the first selectable button to the cloud platform;
   responsive to receiving the data indicative of the selection of the first selectable button, transmitting second data to the first electronic device, wherein the second data causes the first electronic device to display a second interface on the display screen of the first electronic device, wherein the second interface comprises identifiers for pharmacies that are available to fill the first electronic prescription, wherein the first electronic device receives a selection of an identifier for a first pharmacy in the identifiers for the pharmacies, thereby causing the first electronic device to transmit the identifier for the first pharmacy to the cloud platform;
   responsive to receiving the identifier for the first pharmacy from the first electronic device, transmitting the first electronic prescription to a third electronic device of the first pharmacy;
   receiving, at the cloud platform from the third electronic device of the first pharmacy, data indicating that the first electronic prescription has been filled;
   receiving, at the cloud platform from the second ePrescribing application, a second electronic prescription for the second patient prescribed by a second healthcare provider;
   transmitting third data to the second electronic device causing a third interface to be displayed on a display screen of the second electronic device, wherein the third interface comprises:
      a third selectable button indicating that the second electronic prescription is to be transmitted by the cloud platform to the pharmacy and a fourth selectable button indicating that a scannable copy of the second electronic prescription is to be transmitted by the cloud platform to the second electronic device, wherein the second electronic device receives a selection of the fourth selectable button causing the second electronic device to transmit data indicative of the selection of the fourth selectable button to the cloud platform;

transmitting fourth data to the second electronic device, wherein the fourth data causes the second electronic device to display a fourth interface on the display screen of the second electronic device, wherein the fourth interface comprises a scannable copy of the second electronic prescription including a scannable portion configured to provide identifying data for the second electronic prescription, and further wherein an electronic scanner of a second pharmacy scans the scannable portion of the scannable copy of the second electronic prescription;

receiving, at the cloud platform from a fourth electronic device of the second pharmacy, a request to verify validity of the second electronic prescription based on the identifying data for the second electronic prescription, wherein the request includes the identifying data for the second electronic prescription;

responsive to verifying the second electronic prescription, communicating, from the cloud platform to the fourth electronic device of the second pharmacy, an indication that the second electronic prescription is valid;

receiving, at the cloud platform from the fourth electronic device of the second pharmacy, data indicating that the second electronic prescription has been filled by the second pharmacy.

9. A cloud platform that is in network communication with an ePrescribing application and a first electronic device operated by a patient, the cloud platform comprising:

a processor; and memory storing instructions, wherein the instructions, when executed by the processor, cause the processor to perform acts comprising:

receiving, at the cloud platform from the ePrescribing application, an electronic prescription for the patient prescribed by a healthcare provider;

transmitting first data to the first electronic device, wherein the first data causes a first interface to be displayed on a display screen of the first electronic device, wherein the first interface comprises:

a first selectable button indicating that the electronic prescription is to be transmitted by the cloud platform to a pharmacy; and a second selectable button indicating that a scannable copy of the electronic prescription is to be transmitted by the cloud platform to the first electronic device, wherein the first electronic device receives a selection of the second selectable button causing the first electronic device to transmit data indicative of the selection of the second selectable button to the cloud platform;

transmitting second data to the first electronic device, wherein the second data causes the first electronic device to display a second interface on the display screen, wherein the second interface comprises a scannable copy of the electronic prescription including a scannable portion configured to provide identifying data for the electronic prescription, and further wherein an electronic scanner of a first pharmacy scans the scannable portion of the scannable copy of the electronic prescription;

receiving, at the cloud platform from a second electronic device of the first pharmacy, a request to verify validity of the electronic prescription based on the identifying data for the electronic prescription, wherein the request includes the identifying data for the electronic prescription;

responsive to verifying the electronic prescription, communicating, from the cloud platform to the second electronic device of the first pharmacy, an indication that the electronic prescription is valid; and receiving, at the cloud platform from the second electronic device of the first pharmacy, data indicating that the electronic prescription has been filled by the first pharmacy.

10. The cloud platform of claim 9, wherein the first electronic device comprises a desktop computer.

11. The cloud platform of claim 9, wherein the first electronic device comprises a laptop computer.

12. The cloud platform of claim 9, wherein the first electronic device comprises a tablet.

13. The cloud platform of claim 9, wherein the first electronic device comprises a phone.

14. The cloud platform of claim 9, wherein the first interface and the second interface are interfaces of a web portal.

15. The cloud platform of claim 9, wherein the first interface and the second interface are interfaces of a mobile application executing on the electronic device operated by the patient.

16. The cloud platform of claim 9, wherein the first pharmacy comprises a brick and mortar pharmacy.

17. The cloud platform of claim 9, wherein the first pharmacy comprises a mail order pharmacy.

18. The cloud platform of claim 9, wherein the first pharmacy comprises an online pharmacy.

19. The cloud platform of claim 9, wherein the first pharmacy comprises a chain pharmacy.

20. The cloud platform of claim 9, wherein the first pharmacy comprises a particular store of a chain pharmacy.

* * * * *